(12) United States Patent
Schmidt et al.

(10) Patent No.: US 7,157,623 B2
(45) Date of Patent: Jan. 2, 2007

(54) TRANSGENIC MAIZE ENCODING AN ENDOSPERM SPECIFIC PROLAMIN BOX BINDING FACTOR PEPTIDE, WHICH PRODUCES SEED WITH INCREASED METHIONINE OR LYSINE CONENT

(75) Inventors: Robert J. Schmidt, San Diego, CA (US); Stephen P. Moose, Bondville, IL (US); Jesus Vicente-Carbajosa, Madrid (ES)

(73) Assignee: Regents of the University of California, San Diego, La Jolla, CA (US)

( * ) Notice: Subject to any disclaimer, the term of this patent is extended or adjusted under 35 U.S.C. 154(b) by 230 days.

(21) Appl. No.: 10/190,438

(22) Filed: Jul. 3, 2002

(65) Prior Publication Data

US 2003/0051272 A1 Mar. 13, 2003

Related U.S. Application Data

(63) Continuation of application No. PCT/US00/35185, filed on Dec. 22, 2000.

(60) Provisional application No. 60/174,403, filed on Jan. 5, 2000.

(51) Int. Cl.
*A01H 5/00* (2006.01)

(52) U.S. Cl. .................................. 800/320.1
(58) Field of Classification Search .............. 800/320.1
See application file for complete search history.

(56) References Cited

U.S. PATENT DOCUMENTS 5,508,468 A 4/1996 Lundquist et al. .......... 800/205

5,990,384 A 11/1999 Bagga et al. ............... 800/278

OTHER PUBLICATIONS

Yanagisawa et al., Involvement of Maize Dof Zinc Finger Proteins In Tissue-Specific and Light-Regulated gene Expression, The Plant Cell, 1998, 10:75-89.*
Mena, Montana.,et al. ,"An endosperm-specific DOF protein from barley, highly conserved in wheat, binds to and activates transcription from the prolamin-box of a native B-hordein promoter in barley endosperm", *Plant Journal*, vol. 16, No. 1, XP002165470, (Oct. 1998),53-62.
Vicente-Carbajosa, Jesus., et al. ,"A maize zinc-finger protein binds the prolamin box in zein gene promoters and interacts with the basic leucine zipper transcriptional activator Opaque2", *Proceedings of the Nat'l Aca of Sciences of the US*, vol. 94, No. 14, XP002165471, (1997),7685-7690.
Wang, Zhendong.,et al. ,"Characterization of the maize prolamin box-binding factor-1 (PBF-1) and its role in the developmental regulation of the zein multigene family", *Gene, NL, Elsevier Biomedical Press*, Amsterdam, vol. 223, No. 1-2, XP004153604, (Nov. 26, 1998),321-332.
Wang, Zhendong.,et al. ,"Modulation of gene expression by DNA-Protein and protein—protein interactions in the promoter region of the zein multigene family", *Gene, NL, Elsevier Biomedical Press*, Amsterdam, vol. 223, No. 1-2, XP004153605, (Nov. 26, 1998),333-345.

* cited by examiner

*Primary Examiner*—Elizabeth F. McElwain
(74) *Attorney, Agent, or Firm*—Schwegman, Lundberg, Woessner & Kluth, P.A.

(57) ABSTRACT

The invention provides a fertile transgenic monocot, e.g., maize, plant encoding an endosperm specific prolamin box binding factor peptide (PBF) that is expressed so as to increase the methionine and/or lysine content of the seeds of said plant over said content in the seeds of the corresponding plant that lacks said gene, wherein said corresponding plant was used to prepare said transgenic plant, or an ancestor of said transgenic plant.

6 Claims, 3 Drawing Sheets

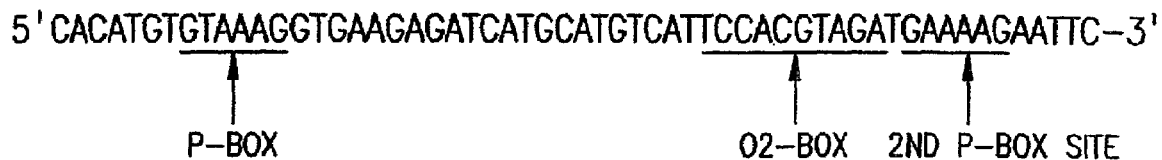

5'CACATGTGTAAAGGTGAAGAGATCATGCATGTCATTCCACGTAGATGAAAAGAATTC-3'

P-BOX          O2-BOX   2ND P-BOX SITE

FIG. 1

| CEREAL/GENE | PROLAMIN BOX SEQUENCE | LOCATION |
|---|---|---|
| Maize | | |
|   22-kD Zein | ACATGTGTAAAGGTGAA | -330 |
|   19-kD Zein | ACATGTGTAAAGGTATT | -326 |
|   15-kD Zein | TGACATGTAAAGTTGAT | -210 |
|   27-kD Zein | TGACGTGTAAAGTAAAT | -352 |
|   10-kD Zein | AGAGGTGTAAATGGTAC | -542 |
| Coix | | |
|   α-Coixin | ACGTATGTAAAGGTGAA | -330 |
| Sorghum | | |
|   γ-Kafirin | TGACGTGTAAAGGTGAA | -339 |
| Barley | | |
|   B-Hordein | TGACATGTAAAGTGAAT | -300 |
|   C-Hordein | TGTAGTGTAAAGTAAAA | -317 |
|   γ-Hordein | TGAGATGTAAAGTGAAT | -297 |
|   D-Hordein | TGTTTTGCAAAGCTCCA | -242 |
| Wheat | | |
|   α-Gliadin | TGAGCTGTAAAGTGAAT | -315 |
|   LMW-Glutenin | TGACATGTAAAGTTAAT | -303 |
|   HMW-Glutenin | TGTTTTGCAAAGCTCCA | -242 |
| Rye | | |
|   α-Secalin | TGTAGTGTAAAGTGAAA | -319 |
| Oat | | |
|   Avenin | TGACATGTAAAGCGAAA | -326 |
| Rice | | |
|   GluB-Glutelin | TGCCATGTAAAGATGAC | -458 |

FIG. 2

```
            Cys-Cys ..... Klas Finger ..... Cys-Cys
PBF         CPRCDSNNTKFCYYNNYSMSQPRYFCKACRRYWTHGGTLRNVPIGGGCRK OBP1        ****s*******nfh*************DV*t

NTBBF1      ****N*t**********lT***G**eS***Vss**

MNB1A       ****a*rD**********nt****h***G******K********V***t**
                 ----->              ----->
ZMDOF2      ****q*rD********nthlS****KS***V*t**

ZMDOF3      ****t***FlT*hR****RA***V*y*R
```

TRANSGENIC MAIZE ENCODING AN ENDOSPERM SPECIFIC PROLAMIN BOX BINDING FACTOR PEPTIDE, WHICH PRODUCES SEED WITH INCREASED METHIONINE OR LYSINE CONENT

RELATED APPLICATIONS

This application is a continuation under 35 U.S.C. 111(a) from International Application No. PCT/US00/35185 filed Dec. 22, 2000 and published in English as WO 01/49852 A1 on Jul. 12, 2001, which claimed priority from U.S. Provisional Application Ser. No. 60/174,403 filed Jan. 5, 2000, which applications are incorporated herein by reference.

BACKGROUND OF THE INVENTION

Human food and animal feed derived from many grains are deficient in a number of the ten essential amino acids which are required in the animal diet. Of importance in improving food or feed value of the cereal grain crops is the ability to manipulate genes encoding proteins that contain high levels of essential amino acids. For example, to be nutritionally adequate and support optimal growth of chickens, corn-soybean meal poultry feed is generally supplemented with synthetic methionine or a methionine analog. The development of lines of corn which supply higher levels of methionine can reduce the need for methionine supplements.

Lysine, an amino acid essential in the diets of humans and monogastric animals, is among the three most limiting amino acids in most of the staple crops, the cereals in particular. Consequently, grain-based diets must be supplemented with synthetic lysine or with lysine-containing oilseed protein meals. Further, since most oilseed meals are themselves inadequate lysine sources, balancing the feed mixture for lysine frequently results in meals which are too high in other, less desirable nutrients. Therefore, a method to increase the lysine content of either the cereal grains or the oilseed crops of both would result in significant added nutritional value, as well as a significant cost savings to end users such as the swine and poultry producers.

Plant breeders have long been interested in using naturally occurring variations to improve protein quality and quantity in crop plants. Maize lines containing higher than normal levels of lysine (70%) have been identified (Mertz et al., *Science*, 145, 279 (1964); Mertz et al., *Science*, 150, 1469 (1965)). However, these lines which incorporate a mutant gene, opaque-2, exhibit poor agronomic qualities, such as reduction in yield, slower drying and increased storage problems, and thus are not commercially useful (Deutscher, *Adv. Exp. Medicine and Biology*, 105, 281 (1978)). Quality Protein Maize (QPM) bred at CIMMYT using the opaque-2 and sugary-2 genes and associated modifiers has a hard endosperm and enriched levels of lysine and tryptophan in the kernels (S. K. Vasal et al., *Proceedings of the 3rd seed protein symposium*, Gatersleben, Aug. 31–Sep. 2, 1983). However, the gene pools represented in the QPM lines are tropical and subtropical. Quality Protein Maize is a genetically complex trait and the existing lines are not easily adapted to the dent germplasm in use in the United States, thus preventing the adoption of QPM by corn breeders.

The amino acid content of seeds is determined primarily (90–99%) by the amino acid composition of the proteins in the seed and to a lesser extent (1–10%) by the free amino acid pools. The quantity of total protein in seeds varies from about 10% of the dry weight in cereals to 20–40% of the dry weight of legumes. Much of the protein-bound amino acids is contained in the seed storage proteins which are synthesized during seed development and which serve as a major nutrient reserve following germination. In many seeds the storage proteins account for 50% or more of the total protein.

To improve the amino acid composition of seeds, genetic engineering technology is being used to isolate, and express genes for storage proteins in transgenic plants. For example, a gene from Brazil nut for a seed 2S albumin composed of 26% sulfur-containing amino acids has been isolated and expressed in the seeds of transformed tobacco under the control of the regulatory sequences from a bean phaseolin storage protein gene. The accumulation of the sulfur-rich protein in the tobacco seeds resulted in an up to 30% increase in the level of methionine in the seeds (Altenbach et al., *Plant Mol. Biol.*, 13, 513 (1989)). However, the potential for allergic reactions in humans exposed to this heterologous protein has limited use of this approach.

The *E. coli* dapA gene encodes a DHDPS enzyme that is about 20-fold less sensitive to inhibition by lysine than a typical plant DHDPS enzyme, e.g., wheat germ DHDPS. The *E. coli* dapA gene has been linked to the 35S promoter of Cauliflower Mosaic Virus and a plant chloroplast transit sequence. The chimeric gene was introduced into tobacco cells via transformation and shown to cause a substantial increase in free lysine levels in leaves (Glassman et al., U.S. Pat. No. 5,258,300; Shaul et al., *Plant Jour.*, 2, 203 (1992); Galili et al., EPO Patent Appl. 91119328.2 (1992)).

The 10 kD-zein storage protein is produced in the endosperm of the maize kernel and contains extremely high levels of methionine (22.5%). It is encoded by the Zps10/(22) gene (M. S. Benner et al., *Theor. Appl. Genet.*, 78 761 (1989). Thus, increased expression of this gene can be used to increase the methionine content of corn. Introduction of exogenous genes into monocots such as the cereal plants has proven to be scientifically more challenging than the transformation of dicots. Lundquist et al. (U.S. Pat. No. 5,508,468) disclose production of transgenic maize expressing the maize 10 kD-zein gene by microprojectile bombardment of regenerable maize cells with a chimeric construct comprising the coding region of this gene. However, from a practical standpoint, approaches based on increasing the total protein content of maize are limited by the nitrogen requirements, cost and lower productivity, and the actual pathogen resistance and hardiness of the resulting high protein variants.

Therefore, a need exists for methods to selectively increase the content of amino acids such as by increasing high methionine or high lysine proteins in maize and other cereal (monocot) plants.

SUMMARY OF THE INVENTION

The present invention provides a transgenic monocot plant, such as a maize plant comprising an isolated DNA sequence, preferably operably linked to a constitutive promoter, which is expressed to yield a prolamin box binding factor peptide (PBF), or a subunit thereof, so as to elevate the level of a preselected amino acid, such as lysine and/or methionine, in the seed of the plant. The PBF or PBF subunit can bind to the promoter regions of seed storage protein genes, such as the 22-kD α-zein and 27-kD γ-zein maize genes, so as to enhance the production of γ-zein, and lower the production of α-zein. In the case of maize, this binding increases the methionine and/or the lysine content of the seeds of said plant over the content in the seeds of the corresponding untransformed (native) maize plant. This beneficial alteration can occur without substantially altering the total protein content of the seed, which can be deleterious to other agronomic characteristics of the transgenic plant. The transgenic maize plants of the present invention include the progeny of the F1 generation transgenic plants and their plant parts, including seeds, leaves, pollen, and the like.

The term "corresponding untransformed plant" refers to a plant of a similar genetic background that lacks the transgene, e.g., the plant that was used as "starting material" to prepare the transgenic plant or a transgenic ancestor of the transgenic plant.

The PBF protein is a novel endosperm-specific, cys2-cys2 zinc finger-type DNA binding protein of the DOF family. It forms protein-protein contacts with the regulatory gene product Opaque-2 (O2) and binds a promoter element (the prolamine box) located two helical turns upstream of the O2 binding site in zein gene promoters. The prolamine box (P-box) has the sequence 5'-TGTAAAG-3'. It has long been implicated as an important cis-regulating element in prolamine storage protein genes of all cereals, such as oats, rice, wheat, millet, barley and sorghum, as well as maize, due to its conservation in both sequence and position among prolamine gene promoters. Such binding sites are characterized by an AAAG core. The preferred binding site for PBF is 5'-NTAAAG-3', but is will also bind to 5'-NAAAAG-3', albeit less strongly. The preferred site is present in the P-box, but the second (less strongly bound site) site is present just 3' of the O2-box, as shown in FIG. 1. Such binding sites are both characterized by an AAAG core. See S. Yanagisawa et al., *Plant J.*, 17, 209 (1999).

Using maize endosperm-derived suspension cells in transient assays of 22 kD-zein gene activation, a requirement for both the P-box and O2-box sequences for O2-dependent activation of the 22 kD zein gene promoter has been demonstrated. In this system, it has been shown that O2 activates the promoter by specific binding at the O2-box, but is dependent on the presence of the P-box (presumably due to the binding of PBF to this site). Surprisingly, in this same system overexpression of PBF inhibits O2-dependent activation of the 22-kD zein promoter. This is inconsistent with the earlier observation that the P-box sequence was essential for high levels of promoter activity.

Overexpression of the maize PBF gene in maize endosperm results in up-regulation of the 27-kD (γ-zein) promoter while simultaneously down-regulating expression of the 22-kD (α-zein) promoters. Considering that in normal maize the α-zein represents about 70% of the total zein protein while γ-zein is only about 10%, up-regulation of γ-zein while simultaneously repressing expression of the α-zein can lead to a dramatic shift in the relative abundance of these different zein proteins. Since the γ-zein has a sulfur-containing amino acid content that is 3× greater than that of α-zein, and since reduced α-zein results in an overall increased seed lysine content, this can result in a significant improvement in the quality of the endosperm protein in maize.

The present invention thus also provides a method for preparing a transgenic monocot plant comprising a recombinant Dof gene, such as the PBF gene, that is expressed so as to alter the seed storage protein profile and, thus, the amino acid profile, e.g., to increase the methionine and/or lysine content of the seeds of said transgenic plant over said content in the seeds of the corresponding plant that lacks said gene. For example, the method comprises introducing into regenerable monocot cells, an isolated DNA sequence comprising a PBF gene operably linked to a promoter functional in said cells, and regenerating fertile transgenic plants from said cells, wherein the cells of said plant express a PBF peptide that alters the profile of seed storage proteins, e.g., that enhances the production of γ-zein and lowers the production of α-zein in maize, or that activates hordein gene expression in barley or glutenin expression in wheat. The transgene is heritable in that it can be transmitted to progeny plants via normal sexual reproduction, and introduced into hybrid or inbred lines by conventional plant breeding techniques, so as to improve the amino acid profile of subsequent generations.

Finally, the promoter of the methionine-rich 15-kD zein (16% sulfur-containing amino acids) contains the highly conserved P-box site and can be positively activated by a transgene expressing PBF. Therefore, the present invention also provides transgenic maize over expressing PBF that can yield seeds with a further incremented increased methionine content due to elevated levels of 15-kD zein.

BRIEF DESCRIPTION OF THE FIGURES

FIG. 1 is the sequence of a portion of the 22-kD α-zein gene promoter from position −330 to −274 relative to the initiation codon. (SEQ ID NO:1) The location of the P-box (PBF-binding site), O-2 box (O2 binding site) and lower capacity PBF binding site (2d P-box site) are underlined.

FIG. 2 depicts the alignment of cereal seed storage protein gene promoters in the region of the P-box sequence element. (SEQ ID NOs 2–18; SEQ ID NO:2 corresponds to the P-box sequence for maize 22-kDa zein; SEQ ID NO:3 corresponds to the P-box sequence for maize 19-kDa zein; SEQ ID NO:4 corresponds to the P-box sequence for maize 15-kDa zein; SEQ ID NO:5 corresponds to the P-box sequence for maize 27-kDa zein; SEQ ID NO:6 corresponds to the P-box sequence for maize 10-kDa zein; SEQ ID NO:7 corresponds to the P-box sequence for coix α-coixin; SEQ ID NO:8 corresponds to the P-box sequence for sorghum γ-kafirin; SEQ ID NO:9 corresponds to the P-box sequence for barley B-hordein; SEQ ID NO:10 corresponds to the P-box sequence for barley C-hordein; SEQ ID NO:11 corresponds to the P-box sequence for barley γ-hordein; SEQ ID NO:12 corresponds to the P-box sequence for barley D-hordein; SEQ ID NO:13 corresponds to the P-box sequence for wheat α-gliadin; SEQ ID NO:14 corresponds to the P-box sequence for wheat LMW glutenin; SEQ ID NO:15 corresponds to the P-box sequence for wheat HMW glutenin; SEQ ID NO:16 corresponds to the P-box sequence for rye ω-secalin; SEQ ID NO:17 corresponds to the P-box sequence for oat avenin; SEQ ID NO:18 corresponds to the P-box sequence for rice GluB glutelin). The location of each P-box element is given in nucleotides upstream of the translation start codon. GenBank accession numbers for the different promoter sequences are in parentheses: 22-kDa zein (X55722), 19-kDa zein (V01472), 15-kDa zein (M13507), 27-kDa zein (X58197), 10-kDa zein (M23537), α-coixin (X63113), γ-kafirin (X62480), B-hordein (X87232), C-hordein (M36941), γ-hordein (M36378), D-hordein (X84368), α-gliadin (K03076), LMW glutenin (X07747), HMW glutenin (X12929), ω-secalin (X60295), avenin (J05486), and GluB glutelin (X54193).

DETAILED DESCRIPTION OF THE INVENTION

A. Introduction

Figure 3:
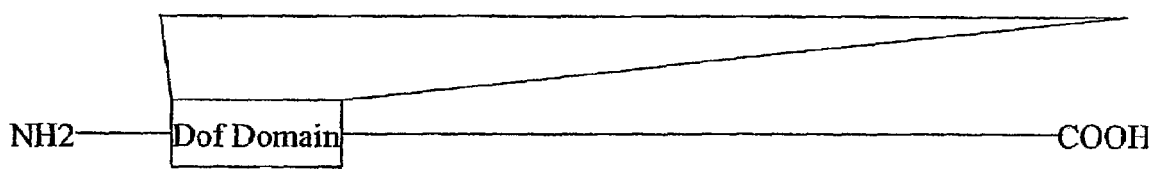
FIG. 3 depicts alignment of Dof peptide domains encoded by maize (PBF (SEQ ID NO:19), MNB1a (SEQ ID NO:22) (B. Zhang et al., *Plant Cell,* 7, 2241 (1995)), ZMDOF2 (SEQ ID NO:23) (T. Quayle et al., *Mol. Gen. Genet.,* 23, 369 (1992)), ZMDOF3 (SEQ ID NO:24) (T. Quayle et al., *Mol. Gen. Genet.,* 23, 369 (1992)), *Arabidopsis* (OBP1)(SEQ ID NO:20) (S. Yanagisawa, *Trends Plant Sci.,* 1, 213 (1996)), and tobacco (NTBBF1) (SEQ ID NO:21) (De Paolis et al., *Plant J.*, 10, 215 (1996)) genes. (*) indicate amino acid identity to PBF. Uppercase letters indicate conservative substitutions, whereas lowercase letters denote nonconservative substitutions. The Dof domain is located at the amino terminus for each of these proteins. The regions corresponding to the primer sequences used in the reverse transcriptase-PCR amplification of the PBF cDNA are underlined with arrows.
Figure 4A:
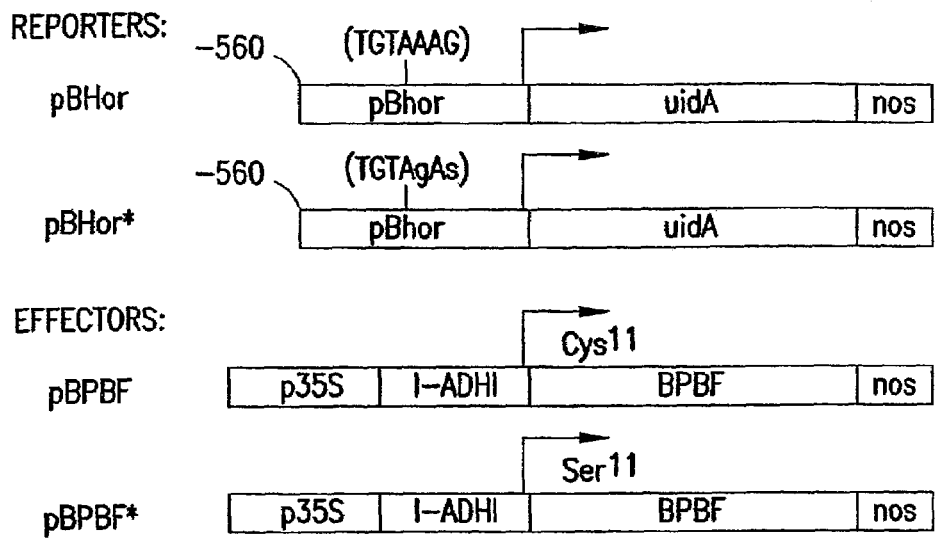
FIG. 4(a) is a diagrammatic structure of the reporter and effector constructs used in the study of BPBF transactivation of a B-hordein promoter through interaction with the P-box element. The pBhor construct contains 560 bp of upstream sequences of the Hor2-184 gene. pBhor* differs from pBhor in the two indicated nucleotide substitutions at the −300 P-box motif. The effector genes were under the control of the CaMV35S promoter followed by the first intron of the maize Adh1 gene. pBPBF contains the whole barley Pbf cDNA. In pBPBF*, the codon for Cys at position 41 in BPBF was mutated to encode a Ser. In all constructs, the nos 3' sequences were included.
Figure 4B:
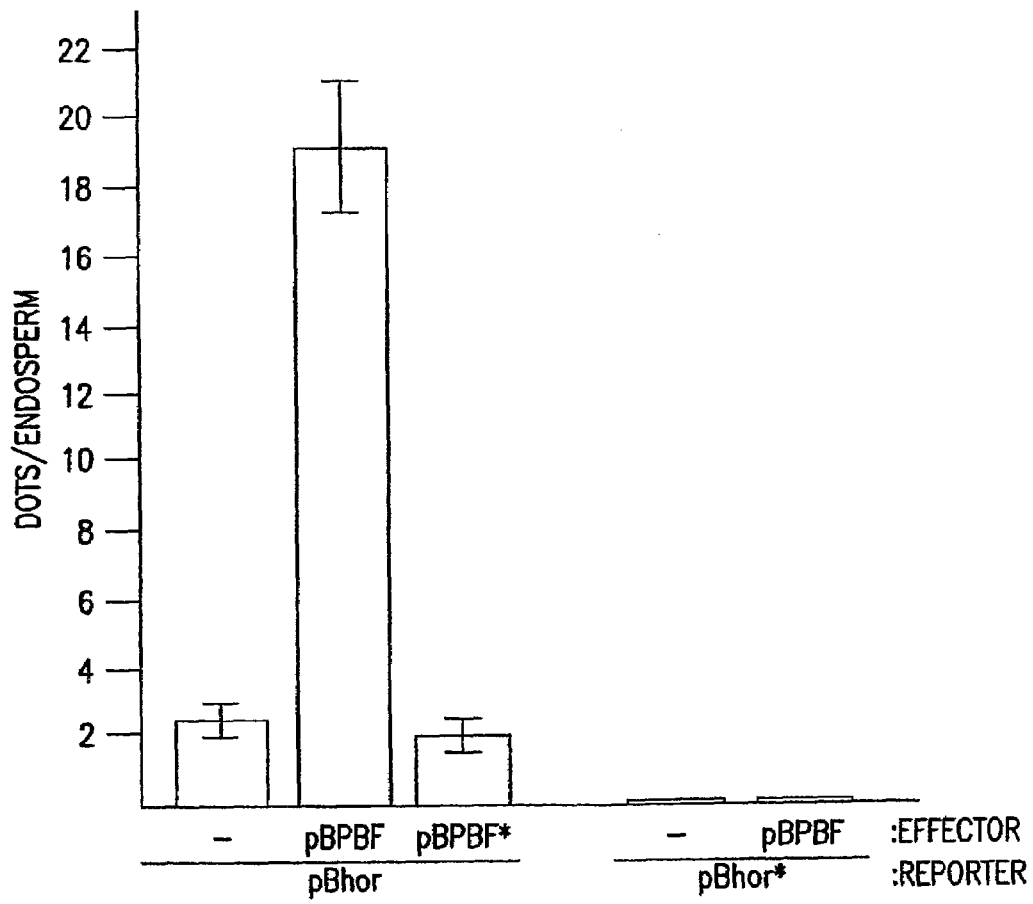
FIG. 4(b) is a graph depicting reporter gene activity following bombardment with the constructs of FIG. 4(a). Isolated developing barley endosperms (approximately 18 d.a.p.) were transfected by particle bombardment with the indicated combinations of reporter and effector plasmids at a 1:1 molar ratio. (−) indicates the absence of the effector pBPBF. β-Glucuronidase activity (GUS) as detected by histochemical staining and subsequent counting of blue dots per endosperm. Column height represents the mean value of three independent experiments. Bars indicate standard errors. In each experiment involving the pBhor plasmid as reporter, sets of five endosperms were bombarded and four replicates were done, while two replicates were performed for the experiments involving pBhor*.

The prolamin seed storage proteins of maize, named zeins, are encoded by five distinct classes of genes that are distinguished by the molecular mass of their protein products (reviewed in G. A. Thompson et al., *BioEssays*, 10, 108 (1984)). Zein gene mRNA and protein expression are limited to the endosperm and coordinately regulated in a temporal fashion, beginning between 8 and 10 days after pollination (DAP), peaking at 16 DAP, and continuing throughout seed development. Though cereal seed storage proteins are the primary source of proteins in human diets worldwide and have long been the subject of intense scientific study, our understanding of the molecular mechanisms regulating their expression is limited. Much of what is known about this process in maize is based on the molecular, genetic, and biochemical analysis of the opaque2 locus. This work has demonstrated that the Opaque2 (O2) gene encodes a basic leucine zipper (bZIP) transcription factor that binds to a promoter element in the 22-kDa class of zein genes to activate their expression. See, e.g., R. J. Schmidt et al., *PNAS USA*, 87, 46 (1990); H. Hastings et al., *EMBO J.*, 8, 2795 (1989); R. J. Schmidt et al., *Plant Cell*, 4, 689 (1992); T. Veda et al., *Plant Cell*, 4, 701 (1992).

The primary effect of the opaque2 mutation is a reduction in the transcription of a specific subset of zein genes. This leads to a corresponding decrease in 22-kDa, and to a lesser extent, 15-kDa zein protein compared with wild type. Consistent with these phenotypic effects, only the 22- and 15-kDa zein gene promoters contain O2 binding sites. Therefore, additional regulatory factors and promoter elements must mediate the coordinate activation of all classes of zein genes during endosperm development.

The prolamin box (P-box) is a good candidate for such a cis-acting regulatory element, because it is present within the promoters of all zein genes as well as many storage protein genes from related cereals (FIG. 2). The P-box was initially identified on the basis of both its highly conserved nucleotide sequence (5'-TGTAAAG-3') and position (−300 region) relative to the translation start codon of prolamin genes (B. G. Forde et al., *Nucl. Acids Res.*, 13, 7327 (1987); J. W. S. Brown et al., *Eur. J. Cell Biol.*, 42, 161 (1986)). Uncharacterized endosperm nuclear factors have been shown to bind the P-box present in the 19-, 22- and 27-kDa zein gene promoters (V.-G. Maier et al., *EMBO J.*, 6, 17 (1987); T. Veda et al., *Mol. Cell. Biol.*, 14, 1994)). Further analysis of these protein-DNA interactions indicate that they may be specific to the endosperm. Transient expression assays of zein gene promoter activity in maize endosperm suspension culture cells suggest that the P-box plays a positive role in the coordinate activation of zein gene expression during endosperm development. T. Veda et al., cited above; T. Quayle et al., *Mol. Gen. Genet.*, 231, 369 (1992). Interestingly, the P-box in the 22-kDa zein gene promoter lies just 20 nucleotides upstream of the binding site for O2, suggesting that O2 may interact with factors binding the P-box to activate 22-kDa zein gene expression (R. J. Schmidt et al., *Plant Cell*, 4, 689 (1992)).

B. DNA Sequences Encoding PBF Peptides

The endosperm-specific maize cDNA (the PBF gene) that encodes prolamin box binding factor peptide, PBF, has been cloned. PBF forms protein-protein contacts in vitro with O2, but not with the related maize bZIP protein OHP1. This indicates that PBF represents the P-box binding activity observed in maize endosperm nuclei, and that specific protein-protein interactions between PBF and O2 are important in the regulation of 22-kDa zein gene expression.

Considering the conserved sequence and position of the P-box among cereal storage protein genes, it is likely that homologous proteins exist in the endosperm of other cereals. The cloning of the maize PBF gene will thus facilitate the isolation of corresponding genes in other important grain crops, by methods corresponding to those set forth below, such as by reverse transcriptase-PCR.

PBF cDNA expressed in *E. coli* was found to produce a peptide that binds to the P-box with the same sequence specificity as the factor identified in maize endosperm. Extensive screening at reduced stringency of the starting maize endosperm cDNA library with the initial reverse transcriptase-PCR product or the cloned PBF cDNA resulted in the isolation of only PBF cDNAs. This indicates that PBF is at least the most abundant, and probably the only, Dof protein gene expressed at significant levels in maize endosperm.

Endosperm nuclear factors that bind the P-box promoter element were one of the first protein-DNA interactions identified in plants. See, V.-G. Maier et al., *EMBO J.*, 6, 17 (1987). However, extensive screens to identify P-box binding proteins from endosperm cDNA expression libraries with labeled P-box probes were unsuccessful. A probable explanation for the failure to identify PBF by this method is the presence of an in-frame stop codon 18-bp upstream of the ATG initiation codon. The position of this stop codon, coupled with the amino-terminal location of the Dof domain within PBF, would greatly reduce the probability of obtaining a cDNA insert that would produce both an in-frame fusion protein and still contain a functional Dof DNA-binding domain.

The association between PBF peptide and O2 observed in vitro represents an important functional interaction in vivo. This is supported by the fact that O2 and PBF are coexpressed specifically in endosperm tissue and exhibit identical patterns of temporal accumulation during endosperm development. Additionally, PBF failed to interact with OHP1, a bZIP factor that is related to and capable of forming heterodimers with O2, but does not activate 22-kDa zein gene expression.

Further evidence for a functional interaction between PBF and O2 comes from transient expression assays of zein promoter/reporter constructs in maize endosperm suspension culture cells. It previously has been shown that 22-kDa zein promoter activity is enhanced on average 5- to 10-fold in response to O2 expressed from an effector plasmid. It has been determined that deletion of the entire P-box element or specific substitutions in the 5'-AAAG-3' sequence motif (to AgAc) greatly reduce the ability of O2 to transactivate the 22-kDa zein gene promoter. These results indicate that the binding of PBF to the P-box is required for O2-dependent activation of reporter gene expression. Similar interactions have been proposed for nuclear factors that bind the P-box and a neighboring bZIP consensus sequence from the wheat glutenin and barley C-hordein storage protein genes.

The early analysis of both 22-kDa and 27-kDa zein gene promoter activity in transient expression assays with endosperm culture cells suggests that factors binding the P-box participate in the coordinate activation of zein genes during endosperm development. At least three observations regarding PBF and the P-box support this view: (i) PBF mRNA is specific to the endosperm and accumulates immediately before the activation of zein gene expression, (ii), PBF specifically interacts with O2, a known activator of zein gene expression, and (iii) the P-box is required for the O2-dependent transactivation of the 22-kDa zein gene promoter in transient expression assays.

One mechanism for PBF action may be the stimulation of O2 binding to its target sites in 22- and 15-kDa zein gene promoters. The Arabidopsis Dof protein OBP1 significantly stimulates the binding of OBF bZIP proteins to the CaMV-35S and GST6 promoters. Because the promoters of the other classes of zein genes lack an O2 binding site, PBF alone may be sufficient to drive their expression, or alternatively PBF may interact with other transcription factors in addition to O2 to coordinately regulate expression of all zein genes.

Mutations in the PBF gene can be obtained through a reverse genetics approach. See, M. Mena et al., *Science* 274, 1537 (1996); R. J. Benson et al., *Plant Cell,* 7, 75 (1995). Also, information relating to the PBF gene DNA sequence, the PBF amino acid sequence and the sequence of other PBF proteins will enable the preparation of cDNA encoding PBF or subunits thereof from other monocot species. For example, a cDNA encoding the barley homolog of maize PBF has been cloned. The barley PBF was found to positively activate the endosperm-specific β-hordein protein promoter via interaction with a prolamin box. M. Mena et al., *Plant J.,* 16, 57 (1998).

Analogs of PBF-encoding DNA that encode PBF mutants that retain or comprise an altered highly conserved Dof 52-amino acid DNA-binding domain, can also be prepared and expressed in monocots, and can yield more selective or tight promoter binding. The $CX_2CX_{21}CX_2C$ (SEQ ID NO:25) motif, wherein X is an amino acid residue, in the Dof domain may form a single zinc finger that is essential for recognition. Also, disruption of DNA binding has been identified in other mutant Dof proteins bearing substituents in the cysteine (C) residue, and by metal chelators that can disrupt zinc coordination. See W. Chen et al., *Plant J.,* 10, 955 (1996); S. Yanagisawa, *Nucl. Acid. Res.,* 23, 3403 (1995).

C. Optional Sequences for Expression Cassettes

1. Promoters

Preferably, the preselected isolated DNA sequences employed in the invention are operably linked to promoters, which provide for expression of the preselected DNA sequence, e.g., as a native PBF or a subunit or mutation (variant) thereof. The promoter is preferably a promoter functional in plants and/or seeds, and more preferably a promoter functional during maize seed development. A preselected DNA sequence is operably linked to the promoter when it is located downstream from the promoter, to form an expression cassette.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. Promoters can also provide for tissue specific or developmental regulation. An isolated promoter sequence that is a strong promoter for heterologous DNAs is advantageous because it provides for a sufficient level of gene expression to allow for easy detection and selection of transformed cells and provides for a high level of gene expression when desired.

Preferred expression cassettes will generally include, but are not limited to, a plant promoter such as the CaMV 35S promoter, or others such as CaMV 19S, nos, Adh, sucrose synthase, α-tubulin, ubiquitin, actin, cab, PEPCase or those associated with the R gene complex. Further suitable promoters include cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene and the actin promoter from rice; seed specific promoters, such as the phaseolin promoter from beans, may also be used. The especially preferred promoter is functional during plant seed development. Other promoters useful in the practice of the invention are known to those of skill in the art.

Alternatively, novel tissue specific promoter sequences may be employed in the practice of the present invention. cDNA clones from a particular tissue are isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

A preselected DNA sequence can be combined with the promoter by standard methods to yield an expression cassette. Briefly, a plasmid containing a promoter such as the 35S CaMV promoter can be constructed or obtained from Clontech Lab in Palo Alto, Calif. (e.g., pBI121 or pBI221). Typically, these plasmids are constructed to have multiple cloning sites having specificity for different restriction enzymes downstream from the promoter. The preselected DNA sequence can be subcloned downstream from the promoter using restriction enzymes and positioned to ensure that the DNA is inserted in proper orientation with respect to the promoter so that the DNA can be expressed as sense or antisense RNA. Once the preselected DNA sequence is operably linked to a promoter, the expression cassette so formed can be subcloned into a plasmid or other vector. Once the preselected sense DNA sequence is obtained, all or a portion of the DNA sequence can be subcloned into an expression vector (see below) in the opposite orientation (i.e., 3' to 5'). The preselected DNA sequence is subcloned downstream from a promoter to form an expression cassette.

In a preferred embodiment, a cDNA clone encoding a PBF or functional subunit or variant is isolated from maize endosperm tissue. This expression cassette can then be subcloned into a vector suitable for transformation of plant cells.

2. Targeting Sequences

Additionally, expression cassettes can be constructed and employed to target the product of the preselected DNA sequence or segment to an intracellular compartment within plant cells or to direct a protein to the extracellular environment. This can generally be achieved by joining a DNA sequence encoding a transit or signal peptide sequence to the coding sequence of the preselected DNA sequence. The resultant transit, or signal, peptide will transport the protein to a particular intracellular, or extracellular destination, respectively, and can then be post-translationally removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3. 3' Sequences

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. Preferred 3' elements are derived from those from the nopaline synthase gene of *Agrobacterium tumefaciens*, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. These 3' nontranslated regulatory sequences can be obtained as described in An (1987) or are already present in plasmids available from commercial sources such as Clontech, Palo Alto, Calif. The 3' nontranslated regulatory sequences can be operably linked to the 3' terminus of the preselected DNA sequence by standard methods.

4. Selectable and Screenable Marker Sequences

In order to improve the ability to identify transformants, one may desire to employ a selectable or screenable marker gene as, or in addition to, the expressible preselected DNA sequence or segment. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Elements of the present disclosure are exemplified in detail through the use of particular marker genes. However in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant cell, e.g., a monocot cell.

Possible selectable markers for use in connection with the present invention include, but are not limited to, a neo gene which codes for kanamycin resistance and can be selected for using kanamycin, G418, and the like; a bar gene which codes for bialaphos resistance; a gene which encodes an altered EPSP synthase protein thus conferring glyphosate resistance; a nitrilase gene such as bxn from *Klebsiella ozaenae* which confers resistance to bromoxynil; a mutant acetolactate synthase gene (ALS) which confers resistance to imidazolinone, sulfonylurea or other ALS-inhibiting chemicals (European Patent Application 154,204); a methotrexate-resistant DHFR gene; a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571, 1987). An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein).

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues; a β-lactamase gene, which encodes an enzyme for which various chromogenic substrates are known (e.g., PADAC, a chromogenic cephalosporin); a xylE gene which encodes a catechol dioxygenase that can convert chromogenic catechols; an α-amylase gene; a tyrosinase gene which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene, which allows for bioluminescence detection; or an aequorin gene, which may be employed in calcium-sensitive bioluminescence detection, or a green fluorescent protein gene (Niedz et al., 1995).

5. Other Optional Sequences

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

I. DNA Delivery of the DNA Molecules into Host Cells

The present invention generally includes steps directed to introducing a preselected isolated DNA sequence, such as a preselected chimeric DNA sequence comprising cDNA, into a recipient cell to create a transformed plant cell. The frequency of occurrence of cells taking up exogenous (foreign) DNA is believed to be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

The invention is directed to any plant species wherein the seed contains storage proteins that contain relatively low levels, or none, of at least one essential amino acid. Cells of the plant tissue source are preferably embryogenic cells or cell-lines that can regenerate fertile transgenic plants and/or seeds. The cells can be derived from either monocotyledons or preferably from dicotyledons. Suitable examples of plant species include wheat, rice, Arabidopsis, tobacco, maize, soybean, and the like. The preferred cell type is a monocotyledon cell such as a maize cell, which may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. Nos. 5,384,253 and 5,472,869, incorporated herein by reference; and direct DNA transfer to plant cells by microprojectile bombardment; U.S. Pat. Nos. 5,489,520, 5,538,877 and 5,538,880, incorporated herein by reference). Methods such as microprojectile bombardment or electroporation can be carried out with "naked" DNA where the expression cassette may be simply carried on any E. coli-derived plasmid cloning vector.

Monocots such as Zea mays and other cereals or grasses can be transformed via microprojectile bombardment of embryogenic callus tissue or immature embryos, or by electroporation following partial enzymatic degradation of the cell wall with a pectinase-containing enzyme (U.S. Pat. Nos. 5,384,253 and 5,472,869). For example, embryogenic cell lines derived from immature Zea mays embryos can be transformed by accelerated particle treatment as described by U.S. Pat. Nos. 5,489,520, 5,538,877 and 5,538,880, cited above. Excised immature embryos can also be used as the target for transformation prior to tissue culture induction, selection and regeneration as described in U.S. patent application Ser. No. 08/112,245 and PCT publication WO 95/06128.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred Zea mays tissue sources. Selection of tissue sources for transformation of monocots is described in detail in U.S. patent application Ser. No. 08/112,245 and PCT publication WO 95/06128 (incorporated herein by reference).

The transformation is carried out under conditions directed to the plant tissue of choice. The plant cells or tissue are exposed to the DNA carrying the preselected DNA sequences for an effective period of time. Buffers and media used will also vary with the plant tissue source and transformation protocol. Many transformation protocols employ a feeder layer of suspended culture cells (tobacco or Black Mexican Sweet, for example) on the surface of solid media plates, separated by a sterile filter paper disk from the plant cells or tissues being transformed.

A. Electroporation

Where one wishes to introduce DNA by means of electroporation, it is contemplated that the method of Krzyzek et al. (U.S. Pat. No. 5,384,253, incorporated herein by reference) will be particularly advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

B. Microprojectile Bombardment

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like. Specific techniques for carrying out microprojectile bombardment of monocots, including maize, are disclosed in U.S. Pat. Nos. 5,538,877 and 6,025,545.

An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension. The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Results from such small scale optimization studies are disclosed herein and the execution of other routine adjustments will be known to those of skill in the art in light of the present disclosure.

II. Production and Characterization of Stable Transgenic Maize

After effecting delivery of a preselected DNA sequence to recipient cells by any of the methods discussed above, the next steps of the invention generally concern identifying the transformed cells for further culturing and plant regeneration. As mentioned above, in order to improve the ability to identify transformants, one may desire to employ a selectable or screenable marker gene as, or in addition to, the expressible preselected DNA sequence. In this case, one would then generally assay the potentially transformed cell population by exposing the cells to a selective agent or agents, or one would screen the cells for the desired marker gene trait.

A. Selection

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0–28 days on nonselective medium and subsequently transferred to medium containing from about 1–3 mg/l bialaphos or about 1–3 mM glyphosate, as appropriate. While ranges of about 1–3 mg/l bialaphos or about 1–3 mM glyphosate will typically be preferred, it is proposed that ranges of at least about 0.1–50 mg/l bialaphos or at least about 0.1–50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of Zea mays L. was selected with sub-lethal levels of bialaphos. Slowly growing tissue was subsequently screened for expression of the luciferase gene and transformants were identified. In this example, neither selection nor screening conditions employed were sufficient in and of themselves to identify transformants. Therefore it is proposed that combinations of selection and screening will enable one to identify transformants in a wider variety of cell and tissue types.

B. Regeneration and Seed Production

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber at about 85% relative humidity, about 600 ppm $CO_2$, and at about 25–250 microeinsteins $m^{-2} \cdot s^{-1}$ of light. Plants are preferably matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con®s. Regenerating plants are preferably grown at about 19° to 28° C. After the regenerating plants have reached the stage of shoot and root development, they may be transferred to a greenhouse for further growth and testing.

Mature plants are then obtained from cell lines that are known to express the trait. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred maize plants in order to introgress the preselected DNA sequence into the genome of the inbred maize plants. This process is referred to as backcross conversion. When a sufficient number of crosses to the recurrent inbred parent have been completed in order to produce a product of the backcross conversion process that is substantially isogenic with the recurrent inbred parent except for the presence of the introduced preselected DNA sequence, the plant is self-pollinated at least once in order to produce a homozygous backcross converted inbred containing the preselected DNA sequence. Progeny of these plants are true breeding and the weight percentage of a particular amino acid in a plant part, e.g., the seeds, in the progeny are compared to the weight percentage of that amino acid in the recurrent parent inbred, in the field under a range of environmental conditions (see below). The determination of the weight percentage of an amino acid or amount of starch are well known in the art.

Alternatively, seed from transformed monocot plants regenerated from transformed tissue cultures is grown in the field and self-pollinated to generate true breeding plants.

Seed from the fertile transgenic plants is then evaluated for the presence and/or expression of the "transgene". Transgenic seed tissue can be analyzed for a substantial inhibition or stimulation in the production of the seed storage protein(s) using standard methods such as SDS polyacrylamide gel electrophoresis. A substantial inhibition of the production of the seed storage protein is a decrease in the weight percent of the seed storage protein, preferably of about 70–100% and more preferably about 80–100% over that normally present in a nontransformed seed. The weight percent of a seed storage protein or an amino acid is based upon the amount of that protein or amino acid present per total weight of all proteins or amino acids in the seed. The seed can also be evaluated for an increase in the weight percent of at least one amino acid essential in the diet of animals by standard methods. An increase in the weight percent of the target amino acid is preferably about 50–300%, and more preferably about 100–200%, over that normally present in the untransformed seed. While not in any way meant to limit the invention, the decrease in the expression in the target seed storage protein is generally accompanied by an increase in other seed storage proteins, or related proteins, having amino acids essential in the diet of animals.

Once a transgenic seed expressing the exogenous DNA sequence and having an increase in the weight percent of one or more of the amino acids essential in the diet of animals is identified, the seed can be used to develop true breeding plants. The true breeding plants are used to develop a line of plants with an increase in the weight percent of an amino acid essential in the diet of animals as a dominant trait while still maintaining other desirable functional agronomic traits. Adding the trait of increasing the weight percent of an amino acid essential in the diet of animals to agronomically elite lines can be accomplished by back-crossing with this trait and with those without the trait and studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not expressing the trait of an increased weight percent of the target amino acid. The resulting progeny are then crossed back to the parent not expressing the trait. The progeny from this cross will also segregate so that some of the progeny carry the trait and some do not. This back-crossing is repeated until the inbred line with the desirable functional agronomic traits, but without the trait of an increase in the weight percent of amino acid(s) essential in the diet of animals, which is expressed in a dominant fashion.

Subsequent to back-crossing, the new transgenic plants are evaluated for an increase in the weight percent of amino acid(s) essential in the diet of animals as well as for a battery of functional agronomic characteristics. These other functional agronomic characteristics include kernel hardness, yield, resistance to disease and insect pests, drought resistance, and herbicide resistance.

Plants that may be improved by these methods include but are not limited to processed plants (canola, potatoes, tomatoes, lupins, sunflower and cottonseed), forage plants (alfalfa, clover and fescue), and, preferably, the grains (maize, wheat, barley, oats, rice, sorghum, millet and rye). The plants or plant parts may be used directly as feed or food or the amino acid(s) may be extracted for use as a feed or food additive.

C. Determination of Stably Transformed Plant Tissues

To confirm the presence of the preselected DNA sequence in the regenerating plants, or seeds or progeny derived from the regenerated plant, a variety of assays may be performed. Such assays include, for example, "molecular biological" assays well known to those of skill in the art, such as Southern and Northern blotting and PCR; "biochemical" assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA sequences or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

III. Increasing the Weight Percent of at Least One Amino Acid Essential to the Diet of Animals The present invention is directed to increasing the amount of an amino acid essential to the diet of animals in a transgenic plant or seed over that normally present in the corresponding nontransformed (nontransgenic) plant or its seed. Plant cells are stably transformed with a preselected DNA sequence comprising a PBF gene or subunit thereof that encodes a proline box binding factor peptide or a functional subunit thereof. The PBF peptide or subunit thereof is expressed in the endosperm in an amount that is effective to alter the seed storage profile of the transgenic plant and its seed, and to thus beneficially alter the amino acid profile of the plant. The transformed cells are used to regenerate fertile transgenic plants and seeds. The DNA sequence is thus expressed in the seeds in an amount effective to enhance the production of a desirable seed storage protein, while preferably inhibiting the production of a second target seed storage protein deficient in the amino acid. The increase in the weight of a minor seed storage protein high in essential amino acids, coupled with the decrease in the seed storage protein deficient in the essential amino acid results in an increase in the weight percent of the target amino acids, preferably essential amino acids, present in other proteins in the transgenic seed over that normally present in the nontransformed seed.

In a preferred embodiment, monocot cell line such as a maize cell line is transformed with an expression vector comprising a preselected DNA sequence encoding all or a functional subunit of a PBF peptide, wherein said PBF peptide binds to the promoter regions of the 22 kD α-zein gene and the promoter region of the 27-kD γ-zein gene, so as to enhance the production of γ-zein and lower the production of the α-zein. Preferably the PBF peptide or subunit is also expressed in an amount sufficient to bind to the 15 kD zein promoter and increase the level of 15 kD zein in the seed. The expression vector preferably further comprises at least one selectable marker gene. The maize cell line is transformed by microprojectile bombardment and transformants are initially selected by growth in the presence of an agent which is present at levels which inhibit the growth of the corresponding nontransformed cells. Transformants are further characterized for the presence or expression of the preselected DNA sequence by polymerase chain reaction (PCR) or reverse transcriptase (RT-PCR) analysis. Transformed maize cell lines having the preselected DNA sequence are used to regenerate fertile transgenic plants by the method as described in PCT publication WO 95/06128. The fertile transgenic plants are self-pollinated or crossed to a second plant variety, and the transgenic seeds are characterized for the stimulation of production of a 27 kD γ-zein and/or the 15 kD zein and the inhibition of production of a 22 kD α-zein protein by quantitative Western blot and for an increase in the weight percent of at least one amino acid essential to the diet of animals, such as lysine or methionine.

The invention will be described by reference to the following detailed examples.

EXAMPLE 1

Cloning of PBF cDNA

A reverse transcriptase-PCR approach was used to isolate Dof-encoding cDNAs from maize endosperm. An oligo(dT) tag primer [5'-GTCGACTCTAGAGGATCC(T)$_{12}$-3'] (SEQ ID NO:26) was used to prime first-strand cDNA synthesis from poly(A)-selected 18-DAP maize endosperm mRNA. The tag primer and two primers derived from conserved residues in the Dof domain (see FIG. 3) were subsequently used in nested PCR amplifications of endosperm cDNA.

DNA sequencing of the amplified products revealed that the primary product contained a Dof-related sequence. This gene fragment was then used as a probe to screen approximately 1×10⁶ plaques of a cDNA library prepared from maize developing endosperm mRNA (M. J. Aukerman et al., Genes Dev., 5, 310 (1991)). Using either standard or reduced stringency hybridization conditions, 20 hybridizing plaques were identified. Eight of these were plaque-purified and determined by restriction mapping and DNA sequencing to represent the same PBF cDNA.

The sequence of this cDNA (deposited in GenBank, accession number U82230) exhibited a high degree of amino acid identity (75–80%) with other Dof domain sequences, but is distinct from previously identified maize Dof genes. The cDNA has the following sequence: cttcttccca gcgacaagag aaaggattag aaaaaggaaa gatccatgga catgatctcc ggcagcactg cagcaacatc aacaccccac aacaaccaac aggcggtgat gttgtcatcc cccattataa aggaggaagc tagggaccca aagcagacac gagccatgcc ccaaataggt ggcagtgggg agcgtaagcc gaggccgcaa ctacctgagg cgctcaagtg cccacgctgc gactccaaca acaccaagtt ttgctactac aacaattata gcatgtcaca accacgctac ttttgcaagg cttgccgccg ctattggaca catggtggta ccctccgcaa tgtccccatt ggtggtgggt gtcgcaagaa caaacatgcc tctagatttg tcttgggctc tcacacctca tcgtcctcat ctgctaccta tgcaccatta tcccctagca ccaacgctag ctctagcaat atgagcatca acaaacatat gatgatggtg cctaacatga cgatgcctac cccaacgaca atgggcttat tccctaatgt gctcccaaca cttatgccga caggtggagg cggggcttt gacttcacta tggacaacca acatagatca ttgtccttca caccaatgtc tctacctagc caggggccag tgcctatgct ggctgcagga gggagtgagg caacaccgtc tttcctagag atgctgagag gagggatttt tcatggtagt agtagctata acacaagtct cacgatgagt ggtggcaaca atggaatgga caagccattt tcgctgccat catatggtgc aatgtgcaca aatgggttga gtggctcaac cactaatgat gccagacaac tggtggggcc tcagcaggat aacaaggcca tcatgaagag cagtaataac aacaatggtg tatcattgtt gaacctctac tggaacaagc acaacaacaa caacaacaac aacaacaaca acaacaacaa caacaacaac aagggacaat aaggttagtg tgccagaccg tggaagcgtt gctgctataa ataatgcaat tgggtagtag tacccagtga aatcaggaga gactagtagc ctagggtgca ttttgattta tttagttttg gtcaagatga caagtcatca tgaatcaccc tttttattca tttgcatgtt ttgtttttt tttttttt (SEQ ID NO:30). The amino acid sequence encoded by the cDNA is MDMISGSTAATSTPHNNQQAVMLSSPII-KEEARDPKQTRAMPQIGGSG ERKPRPQL-PEALKCPRCDSNNTKFCYYNNYSM-SQPRYFCKACRRYWTHGGTLRNVPIG GGCRKNKHASRFVLGSHTSSSSSATYA-PLSPSTNASSSNMSINKHMMMVPNMTMPTPTT MGLFPNVLPTLMPTGGGGGFDFTMDN-QHRSLSFTPMSLPSQGPVPMLAAGGSEATPSFL EML-RGGIFHGSSSYNTSLTMSGGNNGMDK-PFSLPSYGAMCTNGLSGSTTNDARQLVGP QQDNKAIMKSSNNNNGVSLLNLY-WNKHNNNNNNNNNNNNNNNKGQ (SEQ ID NO:29). Outside of the Dof domain, the maize endosperm Dof protein shared no significant amino acid similarity with other Dof proteins. However, the cloned cDNA did show complete sequence identity with a maize EST isolated from an endosperm cDNA library (GenBank accession number T23343).

EXAMPLE 2

Expression of PBF cDNA in E. coli

For expression of PBF in Escherichia coli, the entire PBF cDNA was first cloned into pBluescript KS. The 1,197-bp NcoI-BamHI fragment from this plasmid, with the NcoI site spanning the start codon, was inserted into NcoI+BamHI-digested pET-11d (Novagen) and transformed into E. coli strain BL21(D3). Overnight cultures harboring either the recombinant PBF clone or the pET-11d vector without insert were diluted 1:10 in Luria-Bertani medium and grown for 3 hr at 37° C. PBF expression was then induced with 1 mM isopropyl β-D-thiogalactoside from the phage T7 promoter for 1 hr at 30° C. Cells carrying the pET-11d vector with no insert were similarly induced. Bacterial extracts were prepared by pelleting the cells, sonicating in the presence of lysis buffer (10 mM Hepes, pH 7.9/50 mM KCl/1 mM EDTA/1 mM DTT/0.1 mM phenylmethylsulfonyl fluoride/ 05. mg/ml leupeptin/2 mg/ml aprotinin/10% glycerol) and freezing at −70° C. Five micrograms of total protein from the bacterial extracts was incubated in binding buffer with labeled probes in DNA binding assays.

EXAMPLE 3

DNA-Binding Activity of Recombinant PBF

DNA binding assays were performed essentially as described in R. J. Schmidt et al., Plant Cell, 4, 689 (1992). Three micrograms of protein from endosperm nuclear extracts were incubated in binding buffer at room temperature for 10 min, followed by the addition of 1×10⁵ cpm ³²P-labeled double-stranded DNA probes and incubation at room temperature 20 min. Bound complexes were resolved on nondenaturing 4% polyacrylamide gels in 0.25×TBE (90 mM Tris/64.6 mM boric acid/2.5 mM EDTA, pH 8.3) at 4° C., dried onto Whatman 3MM paper, and autoradiographed.

When the cloned cDNA was expressed in E. Coli and bacterial lysates were tested in electrophoretic mobility-shift assays, the cloned Dof protein specifically bound to the P-box in a manner identical to that observed with endosperm nuclear extracts. The maize Dof protein in the bacterial extracts bound with high affinity to the wild-type P-box probe and demonstrated dramatically increased binding affinity when incubated with the probe containing a tetramer of the P-box core sequence. Similarly, the expressed protein did not bind to the probe where the AAAG sequence motif had been mutated to AgAc. When incubated with the probe containing a mutated TGT sequence, the binding activity of the cloned protein to the probe was reduced in a manner similar to that observed for the endosperm nuclear factor. These results indicate that the cloned maize endosperm Dof cDNA encodes a P-box binding protein that mimics the binding activity of the maize nuclear factor. This protein was therefore named prolamin box binding factor, of PBF.

EXAMPLE 4

PBF mRNA Expression in Endosperm

Because both zein gene expression and the interactions between nuclear factors and the P-box appear to be specific to the endosperm, the expression of PBF might be expected to be endosperm-specific. The spatial distribution of PBF gene expression was examined among each of the major maize organs.

Total RNA was isolated as described by K. C. Cone et al., *PNAS USA,* 83, 9631 (1986) from maize wild-type tissues (inbred Oh43) or mutant endosperm homozygous for the o2-R null allele in an Oh43 background (M. J. Aukerman et al., *Genes Dev.* 5, 310 (1991)). RNAs were prepared from 4-day-old seedling roots, expanding leaves (leaf 10), 1.5-cm immature ears, 1.5-cm immature tassels, 18-DAP embryos, and developing endosperms at 5, 8, 10, 12, 14, 15, 18, 21, and 25 DAP. RNA gel blots were prepared from 10 µg of total RNA, hybridized to random primer-labeled probes, and washed as described in M. Mena et al., *Science,* 274, 1537 (1996). The following gel-purified restriction fragments were used as probes: 720-bp XbaI-SpeI restriction fragment from the cloned PBF cDNA, the entire O2 cDNA (R. J. Schmidt, cited above), and a 653-bp PstI-SacI fragment from the plasmid pSKUBI carrying the maize ubiquitin cDNA (A. H. Christensen et al., *Plant Mol. Biol.,* 12, 619 (1989)).

PBF mRNA was only detected in RNA samples isolated from endosperm tissue. The temporal accumulation of PBF expression during endosperm development was then investigated. PBF expression was first detected at 10 DAP, continued to increase with a peak of 15 DAP, and was maintained throughout the remainder of endosperm development. This profile of expression paralleled that observed for the O2 gene and is consistent with both O2 and PBF being present at significant levels in maize endosperm 1–2 days before the expression of zein gene mRNA, which begins around 12 DAP. PBF expression was also observed to be unaffected by null mutations in O2, which demonstrates that PBF expression is not regulated by O2 activity.

EXAMPLE 5

Transient Gene Expression Assays by Microprojectile Bombardment of Developing Barley Endosperms The functional relevance of the interaction observed in vitro between BPBF and the P-box motif was investigated in vivo by assessing the effect of BPBF on the expression of representative B-hordein promoter by transient expression assays in co-bombarded barley endosperms. FIG. 6(a) depicts the structure of the reporter and effector constructs generated for this study.

The proximal promoter region of the B1 hordein gene represented by the pBHR184 genomic clone (B. G. Forde et al., *Nucl. Acids Res.,* 13, 7327 (1985)) was amplified from barley cv. Bomi total DNA with the primers Bhorf (5'-G CGGCCGCATTCGATGAGTCATGTCATG-3') (SEQ ID NO:27) and Bhorr (5'-GGATCCGGTGGATTGGTGTTAACG-3') (SEQ ID NO:28). The 560 bp resulting PCR fragment carried flanking 5' NotI and 3' BamHI sites that were introduced by the PCR primers (underlined). PCR-generated restriction enzyme sites were used to clone this promoter fragment into pBluescript SK and to subsequently obtain its transcriptional fusion with the β-glucuronidase reporter gene (GUS; Jefferson, *Plant Mol. Biol. Rep.,* 5, 38 (1987)) followed by the 3'-nos terminator, resulting in the pBhor plasmid. To generate the reporter construct pBhor*, the internal XbaI-HpaI portion of this promoter was replaced by the same fragment with a mutated P-box motif. The P-box sequence 5'-AAAG-3' was changed to 5'-AgAc-3' using the recombinant PCR approach described above. In this case, the two external primers were Bhorf and Bhorr, and the two internal overlapping primers were the mtP-box oligonucleotides described in FIG. 5(a) of M. Mena et al., *Plant J.,* 16, 53 (1998).

Effector constructs were derived from the plasmid p35IN, harboring the CaMV35S promoter followed by the first intron of the maize AdhI gene and the 3'-nos terminator in a pBluescript vector. The pBPBF plasmid contained the 1230 bp ExoRI-XhoI barley Pbf cDNA fragment that spans the whole barley Pbf coding region (Mena et al., cited above). The mutant barley Pbf cDNA fragment included in plasmid pGST-mtBPBF was released by BamHI and SalI digest and inserted into p35IN to obtain the PBPBF* plasmid.

Particle bombardment was carried out with a biolistic helium gun device (DuPont PSD-1000) according to Klein et al., *Biotechnology,* 6, 559 (1988). DNA-coated gold particles were prepared by mixing 18 µl of gold suspension (60 mg ml$^{-1}$; 1.0 µm in size), 2 µl (2 µg) of Quiagen prepared plasmid, 25 µl of 2.5 M CaCl$_2$ and 10 µl of 0.1 M spermidine. In all cases, 1 µg of the reporter plasmid was included, and for co-transfections, the reporter was combined with the effector plasmid at 1:1 molar ratio. After vortexing for 1 min, the mixture was incubated on ice for at least 2 min, washed twice with ethanol and finally resuspended in 50 µl of ethanol. For bombardment, rupture disks of 1100 p.s.i. were used and 7 µl of particles, dispersed by brief sonication, were spotted onto macro-carriers. The distance between macro-carrier and sample was set at 6 cm.

Barley developing endosperms of approximately 18 d.a.p. were collected from plants grown in the greenhouse at 18° C. under constant illumination. After a surface sterilization, endosperms were manually isolated and placed on half-strength MS medium supplied with sucrose (15 gl$^{-1}$) and containing 0.4% of Phytagel. Endosperms were shot in sets of five and then incubated at 25° C. for 24 h. GUS expression was determined by histochemical staining for 16 h according to Jefferson, cited above. Blue spots were counted under a dissecting microscope and the GUS activity in each assay was expressed as the mean value of blue spots per endosperm. Results from our laboratory had previously shown that this measure of GUS activity directly correlated with fluorometrically quantitated GUS activity per mg of protein, with a correlation coefficient of 0.96 (Vicente-Carbajosa et al., *Plant J.,* 13, 629 (1998)).

As represented in FIG. 6(b) co-transfection of pBhor and pBPBF resulted in about an eightfold increase in GUS activity over that directed by the pBhor alone. No transactivation by pBPBF was observed from the pBhor* reporter, indicating that barley PBF mediates activation of this B-hordein promoter through the wild-type P-box. In addition, the mutation of the P-box site introduced at the pBhor* plasmid resulted in the loss of detectable transcriptional activity of the Hor2-184 promoter in the endosperm, indicating that this mutation also disrupts the transactivation elicited by the endogenous factor(s) that bind to this site. As shown in FIG. 6(b), the pBPBF* effector plasmid that expressed the same mutant protein (Cys$^{41}$→Ser$^{41}$), previously found to be defective for in vitro DNA-binding, was also unable to transactivate GUS expression from the reporter pBhor. Taken together, these results strongly support a role of the barley PBF in the positive activation of hordein gene expression.

All publications, patents and patent documents cited hereinabove are incorporated by reference herein.

What is claimed is:

1. A transgenic maize plant comprising a recombinant DNA comprising a coding sequence operably linked to a promoter, which is expressed to yield a prolamin box binding factor peptide (PBF) that binds to the promoter regions of the 22-kD α-zein and 27-kD γ-zein genes, so as to enhance the production of γ-zein, and lower the production of α-zein, so that the methionine and lysine content of the seeds of said plant is increased over the content in the seeds of the corresponding untransformed (native) maize plant, wherein the PBF has SEQ ID NO:29.

2. The plant of claim 1 wherein the expression of the PBF in the transgenic plant does not reduce yield, slow drying or increase storage problems of the transgenic plant relative to that of the native plant.

3. The plant of claim 1 wherein the PBF binds to the P-box DNA sequence 5'-TGTAAAG-3'.

4. The plant of claim 3 wherein the α-zein promoter region further comprises an AAAG site 3' to a sequence which binds opaque-2 which is 3' to the P-box DNA sequence.

5. The maize plant of claim 1 which also exhibits increased levels of 15-kD zein.

6. A seed obtained from the plant of claim 1 which seed comprises the recombinant DNA.

* * * * *

UNITED STATES PATENT AND TRADEMARK OFFICE
CERTIFICATE OF CORRECTION

PATENT NO. : 7,157,623 B2
APPLICATION NO. : 10/190438
DATED : January 2, 2007
INVENTOR(S) : Schmidt et al.

It is certified that error appears in the above-identified patent and that said Letters Patent is hereby corrected as shown below:

In columns 31-32, lines 52 (Col. 31) and 40 (Col. 32), in Claim 2, delete "reduce yield, slow drying or increase storage problems of the transgenic plant" and insert -- alter the total protein content in seed of the transgenic plant --, therefor.

Signed and Sealed this

Eighteenth Day of December, 2007

JON W. DUDAS
*Director of the United States Patent and Trademark Office*

SEQUENCE LISTING

<160> NUMBER OF SEQ ID NOS: 28

<210> SEQ ID NO 1
<211> LENGTH: 57
<212> TYPE: DNA
<213> ORGANISM: Zea mays

<400> SEQUENCE: 1
cacatgtgta aaggtgaaga gatcatgcat gtcattccac gtagatgaaa agaattc     57

<210> SEQ ID NO 2
<211> LENGTH: 17
<212> TYPE: DNA
<213> ORGANISM: Zea mays

<400> SEQUENCE: 2
acatgtgtaa aggtgaa                                                  17

<210> SEQ ID NO 3
<211> LENGTH: 17
<212> TYPE: DNA
<213> ORGANISM: Zea mays

<400> SEQUENCE: 3
acatgtgtaa aggtatt                                                  17

<210> SEQ ID NO 4
<211> LENGTH: 17
<212> TYPE: DNA
<213> ORGANISM: Zea mays

<400> SEQUENCE: 4
tgacatgtaa agttgat                                                  17

<210> SEQ ID NO 5
<211> LENGTH: 17
<212> TYPE: DNA
<213> ORGANISM: Zea mays

<400> SEQUENCE: 5
tgacgtgtaa agtaaat                                                  17

<210> SEQ ID NO 6
<211> LENGTH: 17
<212> TYPE: DNA
<213> ORGANISM: Zea mays

<400> SEQUENCE: 6
agaggtgtaa atggtac                                                  17

<210> SEQ ID NO 7
<211> LENGTH: 17
<212> TYPE: DNA
<213> ORGANISM: Coix lacryma-jobi

<400> SEQUENCE: 7
acgtatgtaa aggtgaa                                                  17

<210> SEQ ID NO 8
<211> LENGTH: 17
<212> TYPE: DNA
<213> ORGANISM: Sorghum bicolor -continued

```
<400> SEQUENCE: 8
tgacgtgtaa aggtgaa                                                    17

<210> SEQ ID NO 9
<211> LENGTH: 17
<212> TYPE: DNA
<213> ORGANISM: Hordeum vulgare

<400> SEQUENCE: 9
tgacatgtaa agtgaat                                                    17

<210> SEQ ID NO 10
<211> LENGTH: 17
<212> TYPE: DNA
<213> ORGANISM: Hordeum vulgare

<400> SEQUENCE: 10
tgtagtgtaa agtaaaa                                                    17

<210> SEQ ID NO 11
<211> LENGTH: 17
<212> TYPE: DNA
<213> ORGANISM: Hordeum vulgare

<400> SEQUENCE: 11
tgagatgtaa agtgaat                                                    17

<210> SEQ ID NO 12
<211> LENGTH: 17
<212> TYPE: DNA
<213> ORGANISM: Hordeum vulgare

<400> SEQUENCE: 12
tgttttgcaa agctcca                                                    17

<210> SEQ ID NO 13
<211> LENGTH: 17
<212> TYPE: DNA
<213> ORGANISM: Triticum aestivum

<400> SEQUENCE: 13
tgagctgtaa agtgaat                                                    17

<210> SEQ ID NO 14
<211> LENGTH: 17
<212> TYPE: DNA
<213> ORGANISM: Triticum aestivum

<400> SEQUENCE: 14
tgacatgtaa agttaat                                                    17

<210> SEQ ID NO 15
<211> LENGTH: 17
<212> TYPE: DNA
<213> ORGANISM: Triticum aestivum

<400> SEQUENCE: 15
tgttttgcaa agctcca                                                    17

<210> SEQ ID NO 16
<211> LENGTH: 17
<212> TYPE: DNA
```

<213> ORGANISM: Secale cereale

<400> SEQUENCE: 16
tgtagtgtaa agtgaaa                                                        17

<210> SEQ ID NO 17
<211> LENGTH: 17
<212> TYPE: DNA
<213> ORGANISM: Avena sativa

<400> SEQUENCE: 17
tgacatgtaa agcgaaa                                                        17

<210> SEQ ID NO 18
<211> LENGTH: 17
<212> TYPE: DNA
<213> ORGANISM: Oryza sativa

<400> SEQUENCE: 18
tgccatgtaa agatgac                                                        17

<210> SEQ ID NO 19
<211> LENGTH: 50
<212> TYPE: PRT
<213> ORGANISM: Zea mays

<400> SEQUENCE: 19

Cys Pro Arg Cys Asp Ser Asn Asn Thr Lys Phe Cys Tyr Tyr Asn Asn
1               5                   10                  15

Tyr Ser Met Ser Gln Pro Arg Tyr Phe Cys Lys Ala Cys Arg Arg Tyr
            20                  25                  30

Trp Thr His Gly Gly Thr Leu Arg Asn Val Pro Ile Gly Gly Gly Cys
        35                  40                  45

Arg Lys
    50

<210> SEQ ID NO 20
<211> LENGTH: 50
<212> TYPE: PRT
<213> ORGANISM: Arabidopsis thaliana

<400> SEQUENCE: 20

Cys Pro Arg Cys Asp Ser Ser Asn Thr Lys Phe Cys Tyr Tyr Asn Asn
1               5                   10                  15

Tyr Asn Phe Ser Gln Pro Arg His Phe Cys Lys Ala Cys Arg Arg Tyr
            20                  25                  30

Trp Thr His Gly Gly Thr Leu Arg Asp Val Pro Val Gly Gly Gly Thr
        35                  40                  45

Arg Lys
    50

<210> SEQ ID NO 21
<211> LENGTH: 50
<212> TYPE: PRT
<213> ORGANISM: Nicotiana tabacum

<400> SEQUENCE: 21

Cys Pro Arg Cys Asn Ser Thr Asn Thr Lys Phe Cys Tyr Tyr Asn Asn
1               5                   10                  15

Tyr Ser Leu Thr Gln Pro Arg Tyr Phe Cys Lys Gly Cys Arg Arg Tyr
            20                  25                  30

```
Trp Thr Glu Gly Gly Ser Leu Arg Asn Val Pro Val Gly Gly Ser Ser
            35                  40                  45

Arg Lys
    50

<210> SEQ ID NO 22
<211> LENGTH: 50
<212> TYPE: PRT
<213> ORGANISM: Zea mays

<400> SEQUENCE: 22

Cys Pro Arg Cys Ala Ser Arg Asp Thr Lys Phe Cys Tyr Tyr Asn Asn
 1               5                  10                  15

Tyr Asn Thr Ser Gln Pro Arg His Phe Cys Lys Gly Cys Arg Arg Tyr
            20                  25                  30

Trp Thr Lys Gly Gly Thr Leu Arg Asn Val Pro Val Gly Gly Gly Thr
            35                  40                  45

Arg Lys
    50

<210> SEQ ID NO 23
<211> LENGTH: 50
<212> TYPE: PRT
<213> ORGANISM: Zea mays

<400> SEQUENCE: 23

Cys Pro Arg Cys Gly Ser Arg Asp Thr Lys Phe Cys Tyr Tyr Asn Asn
 1               5                  10                  15

Tyr Asn Thr Ser Gln Pro Arg His Leu Cys Lys Ser Cys Arg Arg Tyr
            20                  25                  30

Trp Thr Lys Gly Gly Ser Leu Arg Asn Val Pro Val Gly Gly Gly Thr
            35                  40                  45

Arg Lys
    50

<210> SEQ ID NO 24
<211> LENGTH: 50
<212> TYPE: PRT
<213> ORGANISM: Zea mays

<400> SEQUENCE: 24

Cys Pro Arg Cys Asp Ser Thr Asn Thr Lys Phe Cys Tyr Phe Asn Asn
 1               5                  10                  15

Tyr Ser Leu Thr Gln Pro Arg His Phe Cys Arg Ala Cys Arg Arg Tyr
            20                  25                  30

Trp Thr Arg Gly Gly Ala Leu Arg Asn Val Pro Val Gly Gly Gly Tyr
            35                  40                  45

Arg Arg
    50

<210> SEQ ID NO 25
<211> LENGTH: 29
<212> TYPE: PRT
<213> ORGANISM: Artificial Sequence
<220> FEATURE:
<223> OTHER INFORMATION: A motif
<221> NAME/KEY: SITE
<222> LOCATION: (1)...(29)
<223> OTHER INFORMATION: Xaa = Any Amino Acid

<400> SEQUENCE: 25
```

```
Cys Xaa Xaa Cys Xaa Xaa Xaa Xaa Xaa Xaa Xaa Xaa Xaa Xaa
 1               5                      10                  15

Xaa Xaa Xaa Xaa Xaa Xaa Xaa Xaa Xaa Cys Xaa Xaa Cys
               20                  25

<210> SEQ ID NO 26
<211> LENGTH: 19
<212> TYPE: DNA
<213> ORGANISM: Artificial Sequence
<220> FEATURE:
<223> OTHER INFORMATION: A primer

<400> SEQUENCE: 26
gtcgactcta gaggatcct                                             19

<210> SEQ ID NO 27
<211> LENGTH: 28
<212> TYPE: DNA
<213> ORGANISM: Artificial Sequence
<220> FEATURE:
<223> OTHER INFORMATION: A primer

<400> SEQUENCE: 27
gcggccgcat tcgatgagtc atgtcatg                                   28

<210> SEQ ID NO 28
<211> LENGTH: 24
<212> TYPE: DNA
<213> ORGANISM: Artificial Sequence
<220> FEATURE:
<223> OTHER INFORMATION: A primer

<400> SEQUENCE: 28
ggatccggtg gattggtgtt aacg                                       24
```